(12) United States Patent
Beyersdorf et al.

(10) Patent No.: US 10,716,608 B2
(45) Date of Patent: Jul. 21, 2020

(54) LOAD DISTRIBUTOR FOR A STERNUM CLOSURE DEVICE AND TOOL FOR CUTTING THE LOAD DISTRIBUTOR

(71) Applicant: Stryker European Holdings I, LLC, Kalamazoo, MI (US)

(72) Inventors: Friedhelm Beyersdorf, Freiburg (DE); Christian Knoepfle, Donaueschingen (DE); Karl Greiner, Muehlheim (DE); Manfred Schmuck, Muehlheim (DE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 431 days.

(21) Appl. No.: 15/461,626

(22) Filed: Mar. 17, 2017

(65) Prior Publication Data

US 2017/0265919 A1 Sep. 21, 2017

(30) Foreign Application Priority Data

Mar. 18, 2016 (EP) ..................................... 16000665

(51) Int. Cl.
*A61B 17/82* (2006.01)
*A61B 17/88* (2006.01)

(52) U.S. Cl.
CPC ........ *A61B 17/823* (2013.01); *A61B 17/8861* (2013.01); *A61B 17/8863* (2013.01)

(58) Field of Classification Search
CPC ... A61B 17/82; A61B 17/823; A61B 17/8861; A61B 17/8863
USPC .................................................. 606/74, 905
See application file for complete search history.

(56) References Cited

U.S. PATENT DOCUMENTS

| 2,279,068 | A | * | 4/1942 | Siebrandt ........... A61B 17/8861 140/121 |
|---|---|---|---|---|
| 5,993,452 | A | | 11/1999 | Vandewalle |
| 6,287,307 | B1 | | 9/2001 | Abboudi |
| 8,597,327 | B2 | | 12/2013 | Stone et al. |
| 2003/0078585 | A1 | | 4/2003 | Johnson et al. |
| 2011/0106153 | A1 | | 5/2011 | Stone et al. |
| 2012/0109129 | A1 | * | 5/2012 | Bernstein ............. A61B 17/823 606/74 |
| 2015/0038969 | A1 | | 2/2015 | Garcia et al. |

FOREIGN PATENT DOCUMENTS

| WO | 2012027025 A2 | 3/2012 |
|---|---|---|
| WO | 2014149244 A1 | 9/2014 |

OTHER PUBLICATIONS

Extended European Search Report for Application No. 16000665.6 dated Sep. 28, 2016.
European Search Report for Application No. EP18169717 dated Aug. 29, 2018.

* cited by examiner

*Primary Examiner* — Si Ming Ku
(74) *Attorney, Agent, or Firm* — Lerner, David, Littenberg, Krumholz & Mentlik, LLP (57) ABSTRACT

A load distributor for a sternum closure device comprises a wire receiving section configured to be attached to a wire of the sternum closure device, and a load distributing section. A tool for cutting the load distributor comprises a pair of jaws movable between a load distributor receiving position and a cutting position, wherein at least one of the jaws has substantially V-shaped cutting edges tapered towards the other jaw in an angle to the longitudinal extension of the tool.

19 Claims, 8 Drawing Sheets

LOAD DISTRIBUTOR FOR A STERNUM CLOSURE DEVICE AND TOOL FOR CUTTING THE LOAD DISTRIBUTOR

CROSS-REFERENCE TO RELATED APPLICATIONS

The present application claims the benefit of European Patent Application No. 16000665.6, filed Mar. 18, 2016, the disclosure of which is hereby incorporated herein by reference.

BACKGROUND OF THE INVENTION

The present disclosure generally relates to surgical devices. In particular, a load distributor for a sternum closure device, a sternum closure device comprising the load distributor, a tool for cutting the load distributor, and a sternum closure system comprising the load distributor and the tool are described.

To promote the healing process of fragmented or cut bone, it has been known to exert an external force on bone parts by tightly clamping them together. To this end, flexible elongated members such as wires can be used which are tensioned around the bone parts.

For example, prior to heart surgery, the sternum bone is often cut into two halves by means of a longitudinal section to obtain access to the heart. The sternum halves later need to be fixedly joined again. This can be done by arranging a wire around the sternum halves in a circumferential manner so as to surround a cross-sectional area thereof. Said cross-sectional area extends typically transverse to the longitudinal section through the sternum. Afterwards, the wire is tensioned and fixed by connecting and twisting the free ends thereof.

Furthermore, it has been known to arrange protector pads between the wire and an adjacent surface of the respective bone fragments. The protector pads avoid that the wire cuts into the bone surface when tensioning it, thus causing damage to the bone.

U.S. Pat. No. 6,287,307 B1 discloses an apparatus and a method for clamping the split bone sections of a sternum. For doing so, protector pads in form of sternal plates are arranged in opposite configuration at the split sternum halves. The sternum plates are provided with spikes which are driven into outer side surfaces of the sternum halves by means of a forceps. The sternum plates are hence directly fixed at the bone fragments in a first step. Afterwards, a surgeon can guide and tension a circumferential wire around the sternum plates and the bone fragments arranged therebetween.

U.S. Pat. No. 8,597,327 B2 teaches a method and apparatus for securing a fractured or sectioned sternum by means of a flexible member construct forming circumferential loops around the sternum halves. In addition, protector members are provided for guiding and fixing said flexible member construct around the sternum halves.

WO 2012/027025 A2 discloses a method for closing a sternum with help of adhesives. The adhesives may also be applied in contact regions between the sternum halves and an additionally provided circumferential wire to form a protective layer similar to the known protector pads.

WO 2014/149244 A1 relates to protective sleeve. A guide wire is movable within the protective sleeve and comprises a stop, such that it can abut on the protective sleeve in order to advance the protective sleeve to a desired resting position. Once this resting position is reached, the guide wire is pulled from the protective sleeve.

BRIEF SUMMARY OF THE INVENTION

There is a need for a sternum closure device and associated parts which can be reliably operated and limit unnecessary damage to the sternum bone.

According one aspect of the present disclosure, a load distributor for a sternum closure device is presented. The load distributor comprises a wire receiving section configured to be attached to a wire of the sternum closure device, the wire receiving section having a first cross-sectional dimension. The load distributor further comprises a load distributing section configured to extend between a sternum bone and the wire, the load distributing section having a bone-contacting region and being made from a flexible material to conform to an outer surface of the sternum bone upon tightening of the wire, wherein the bone-contacting region has a second extension substantially perpendicular to the wire receiving section that exceeds the first cross-sectional dimension.

The wire receiving section may be configured to be attached to the wire such that it cannot be removed from the wire under regular operational conditions (e.g., without rendering one or both of the wire and the wire receiving section functionally inoperable). For example, when attached to the wire the wire receiving section may not be movable in any way relative to the wire. The attachment may be performed using one or more of molding, crimping, gluing, using a form-fil, and so on.

The first cross-sectional dimension of the wire receiving section may essentially be defined by a portion of the wire receiving section intended to receive the wire (e.g., by an internal opening of the wire receiving section intended to accommodate the wire). As such, the first cross-sectional dimension may essentially correspond to a diameter of the wire.

The wire receiving section and the load distributing section may be integrally formed. Alternatively, the wire receiving section and the load distributing section may be separately formed and then joined to each other.

The wire receiving section and the load distributing section may be spaced apart along an extension of the wire. Alternatively, the wire receiving section and the load distributing section may at least partially (e.g., fully) overlap along the extension of the wire.

The wire receiving section may comprise at least one crimpable sleeve defining the first cross-sectional dimension. The sleeve may be intended for being crimped around the wire so as to attach the wire receiving section to the wire. The sleeve may be made from a plastically deformable material, such as metal.

The wire receiving section (e.g., the sleeve) may be circumferentially closed (e.g., it may have a cross-sectional form of an O). Alternatively, the wire receiving section (e.g., the sleeve) may be partially open (e.g., it may have a cross-sectional form of a C).

The sleeve may define an opening for receiving the wire, and the load distributing section may have a wire receiving region that forms an extension of the opening of the sleeve. The wire receiving region of the load distributing section may in such a case be provided in addition to the wire receiving section.

Alternatively, or in addition, the sleeve is molded to the load distributing section. Such molding may be realized by injection molding. In such a case the load distributing section may be made from a moldable material, such as any polymeric material (e.g., plastics).

A center of gravity of the load distributor in a cross-section orthogonal to its longitudinal extension may be off-centered from a center of the wire receiving section. As an example, the center of gravity may be off-centered in a direction away from the bone-contacting region. In certain variants, the off-centered center of gravity may be achieved by the provision of an Ω-shaped cross-section of the load distributor. The cross-section may have smoothened transitions and rounded edges, and may further be closed at its basis.

The load distributing section may comprise segments defining the bone-contacting region. The segments may define a segment row. For example, the segments may be spaced apart from each other along an extension of the load distributing section (i.e., along an extension of the wire). The segments may be separated from each other by indentations in the load distributing section. At least some of the segments may have a substantially rectangular shape, preferably with rounded corners.

The segments may define a segment row with two opposite end segments, wherein segments having the same distance from their next end segment may have an identical marking, and segments having different distances from their next end segment may have different markings. These markings may be in form of a consecutive numbering and/or a color-coding.

One or both of the end segments of the segment row may have pointed shape (e.g., a V-shape) at their side facing away from the adjacent segment. The pointed shape may facilitate the placement of the sternum closure device around sternum bone.

According to a further aspect, a sternum closure device is provided. The device comprises a wire essentially defining the first cross-sectional dimension, and a load distributor as presented herein. The wire receiving section of the load distributor may already be attached to the wire upon production of the sternum closure device or may be provided as a separate component for being attached to the wire by surgical personal prior to implantation of the sternum closure device.

The wire may be provided with a surface feature for engagement by the wire receiving section upon attachment to the wire. This surface feature may take any form, such as a roughened a surface of the wire, one or more indentations in and/or protrusions from the wire surface, and so on.

The wire receiving section may comprise at least one crimpable sleeve that is crimped (e.g., upon production) or provided for being crimped (e.g., by surgical personal) around the wire. This sleeve may be placed in the middle of the load distributor.

Alternatively, the load distributor is molded around the wire. The portion of the load distributor molded around the wire this defines the wire receiving section of the load distributor. The load distributor may only be partially molded around the wire. This partial molding may be in the middle or at least at one of the two ends of the load distributor.

According to a further aspect, a tool for cutting a load distributor is provided. The tool comprises a pair of jaws movable between a first load distributor receiving position and a second load distributor cutting position, wherein, in the second position, the jaws overlap in a longitudinal extension of the tool, and wherein the overlapping jaws define substantially V-shaped cutting edges that taper at an angle along the longitudinal extension of the tool.

The longitudinal extension of the tool may correspond to the extension of the load distributor when arranged between the two jaws for cutting. Upon cutting the load distributor, the wire may or may not be attached thereto. In the second position, the jaws may leave a clearance hole. The clearance hole may be dimensioned to essentially correspond to or slightly exceed the first cross-sectional dimension (e.g., a diameter of the wire). In such a case, the clearance hole may prevent a cutting or damaging of the wire upon cutting the load distributor (i.e., may enable a skinning of the wire in relation to a portion of the load distributor).

The V-shaped cutting edges may be defined by at least one of the jaws. For example, the V-shaped cutting edges may be defined by one jaw or by each jaw. Alternatively, a first cutting edge may be defined by one jaw and a second cutting edge may be defined by the other jaw, wherein the first and second cutting edges together are arranged in the form of a V.

The tool may have an additional crimping section comprising a recess on one jaw and a protrusion on the other jaw, such that the protrusion reaches into the recess in the second position of the jaws. The crimping section may be dimensioned in accordance with the crimpable sleeve of the wire receiving section.

The recess may comprise at least one tapered end part having the same inclination as the pair of cutting edges in the second position of the jaws along the longitudinal extension of the tool.

The jaws of the tool may be L-shaped in the longitudinal extension of the tool. Furthermore, the cutting section and the crimping section of the tool may be arranged on different flanks of the L-shaped tool, such that they are at an angle with regard to each other.

According to a still further aspect, a sternum closure system is provided. The system comprises the load distributor or the sternum closure device presented herein, and the tool presented herein. In such a case the clearance hole may substantially corresponds to the first cross-sectional dimension of the wire receiving section or the wire.

BRIEF DESCRIPTION OF THE DRAWINGS

Further details, advantages and aspects of the present disclosure will become apparent from the following embodiments taken in conjunction with the drawings, wherein.

DETAILED DESCRIPTION

In the following, the same reference numerals will be used to denote the same or similar structural features.

Figure 1:
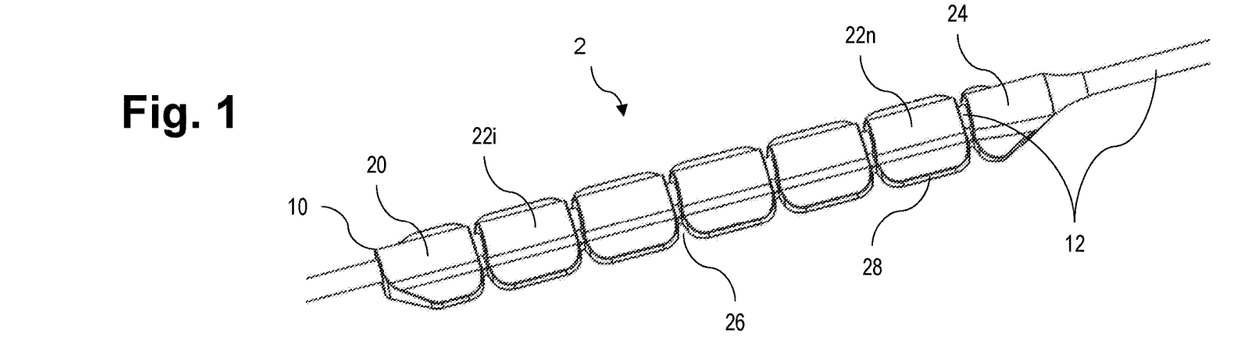
FIG. 1 shows a perspective top view of the sternum closure device according to a first embodiment.
Figure 2:
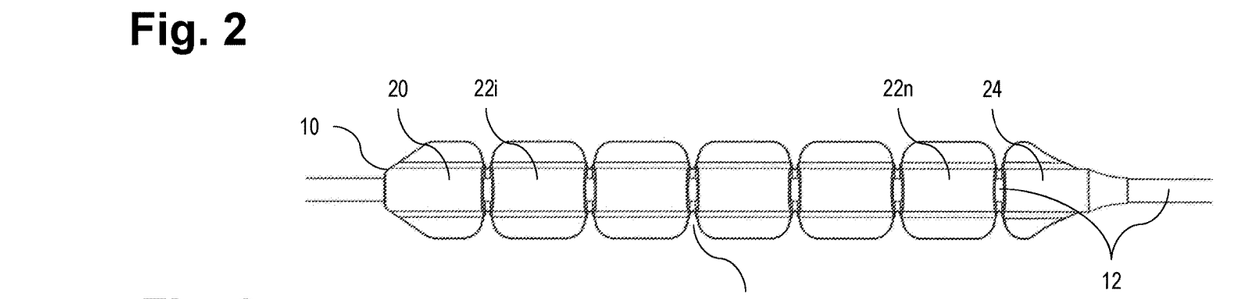
FIGS. 2 and 3 show, respectively, a top, and a bottom view of the sternum closure device in FIG. 1.
Figure 3:
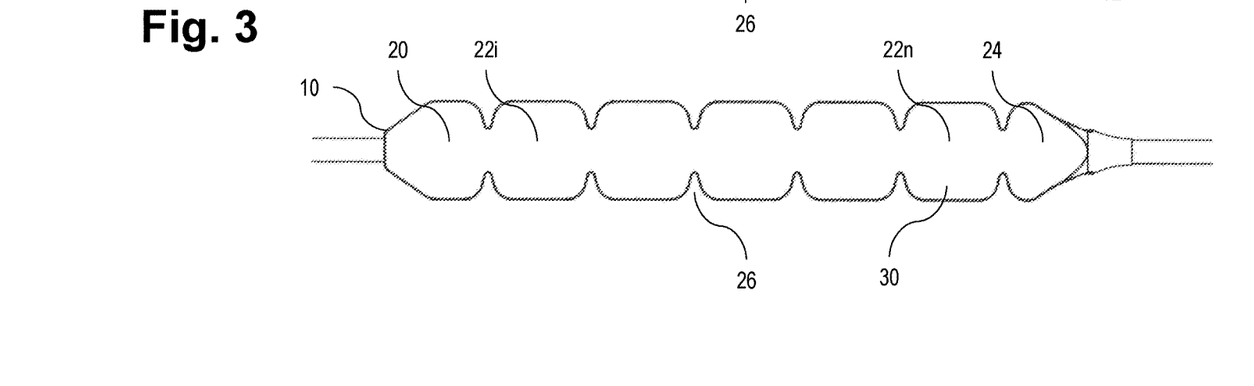

FIGS. 1 to 3 show a sternum closure device 2 having a load distributor 10 and a wire 12 according to a first embodiment. FIGS. 4 to 8 show a sternum closure device 2 according to a modification of the first embodiment. The two variants essentially differ in the shape of the wire 12.

The sternum closure device 2 is configured to be utilized in surgical procedures in which the parts of the segmented sternum are to be fixed together by arranging the sternum closure device 2 in a circumferential manner around the sternum parts so as to achieve a compression force. To maintain a compression force, the free ends of the wire 12 may be fixed relative to each other (e.g, by a knot or a further implant component). In this state, the load distributor 10 prevents a cutting of the wire into the sternum bone as the force exerted by the wire is applied over a larger area.

The wire 12 has in the embodiment of FIGS. 1 to 3 a uniform cross-section and is passing through the load distributor 10. For this purpose the load distributor 10 has a wire receiving section 14 (see FIGS. 5 and 6, but in a similar manner for the variant in FIGS. 1 to 3), which in this case is a cylindrical inner wall 16 having a first cross-sectional dimension and forming a through hole in the longitudinal direction of the load distributor 10. The first cross-sectional extension substantially corresponds to the cross-section of the wire 12.

The wire receiving section 14 of the first embodiment in FIGS. 1 to 6 basically corresponds to the one shown by a side cross-section of a load distributor 100 shown in FIG. 10 and described further below. However, in FIG. 1, the wire receiving section 14 is configured to be attached to the wire 12 by being molded over the wire 12. In order to improve the engagement by the wire receiving section 14 with the wire 12, the wire 12 may be provided with a surface feature such as an increased surface roughness, protrusions, indentations (see FIGS. 7 and 8) or the like.

The load distributor 10 has a load distributing section 28 configured to extend between a sternum bone and the wire 12. The load distributing section 28 has a substantially flat bone-contacting region 30 (see FIG. 3).

In one variant, the load distributing section 28 has a substantially rectangular shape with two straight sides parallel to an extension of the wire 12. In the present embodiments, the load distributing section 28 has optional segments 20, $22i$-$22n$, 24, which define a segment row. In between these segments 20, $22i$-$22n$, 24 there are indentations 26. The segmentation of the load distributor 10 may, for example, be provided to increase the flexibility of the load distributor 10 to conform to the outer surface of sternum bone upon tightening of the wire 12. Of course, this flexibility may additionally or alternatively (i.e., in the absence of a segmentation) be defined by suitably selecting the material or material composition of the load distributor 10.

The two respective outermost of the segments are defined as opposite end segments 20 and 24. The remaining inner segments $22i$-$22n$, in this embodiment i=1 and n=5, have a substantially rectangular outer shape with rounded corners, when viewed from the top or bottom, see FIGS. 2 and 3. The end segments 20 and 24 are tapered from their middle portion in a direction away from the inner segments $22i$-$22n$. Such tapering permits an easier placement of the sternum closure device 2 between a patient's ribs around the sternum bone that is to be fixed and is an optional feature of the device 2.

Further, segments having the same distance from their next end segment 20, 24 may have an identical marking (not shown), and segments having different distances from their next end segment 20, 24 have different markings (not shown). The markings may take the form of printed identifiers (such as numbers) and/or a segment color coding. The markings may be used to symmetrically cut away the same number of segments at opposite ends of the segment row as will be explained below in greater detail.

FIGS. 2 and 3 show, respectively, a top and a bottom view of the sternum closure device in FIG. 1. Here, the segments 20, $22i$-$22n$, 24 and their indentations 26 are better visible than in FIG. 1.

FIG. 3 further shows the bone-contacting region 30 of the load distributing section 28 of the load distributor 10 defined by the bottom surface of the segments 20, $22i$-$22n$, 24. The load distributing section 28 has a second extension substantially perpendicular to the wire receiving section 14 that exceeds the first cross-sectional dimension (i.e., the diameter of the wire 12). As such, a cutting of the wire 12 into the sternum bone upon final placement of the sternum closure device 2 can be prevented.

As shown in FIG. 3, both the minimum second extension in the region of the indentations 26 and the maximum second extension in the region of the segments 20, $22i$-$22n$, 24 exceed the first cross-sectional extension. It will be appreciated that in many situations it will be sufficient if the maximum section extension exceeds the first cross-sectional extension.

Figure 4:
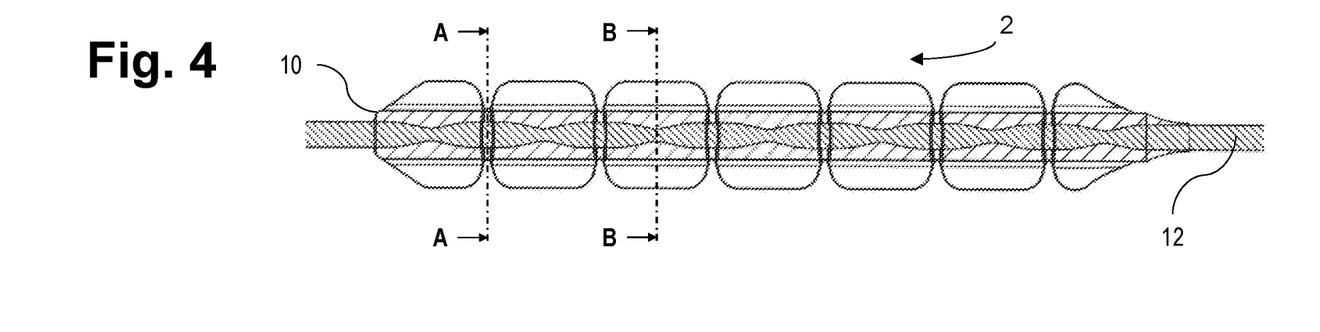
FIG. 4 shows a longitudinal cross-section of a sternum closure device according to a modification of the first embodiment.

FIG. 4 shows a longitudinal cross-section of a sternum closure device 2 according to a modification of the first embodiment. This modification relates to the wire 12, which now has a non-uniform cross-section within the segments 20, $22i$-$22n$, 24. Such a non-uniform cross-section results in a better attachment of the wire 12 to the load distributor 10 in general and to the wire receiving section 14 in particular as the wire cannot easily slip through the wire receiving section 14 in this case.

Figure 5:
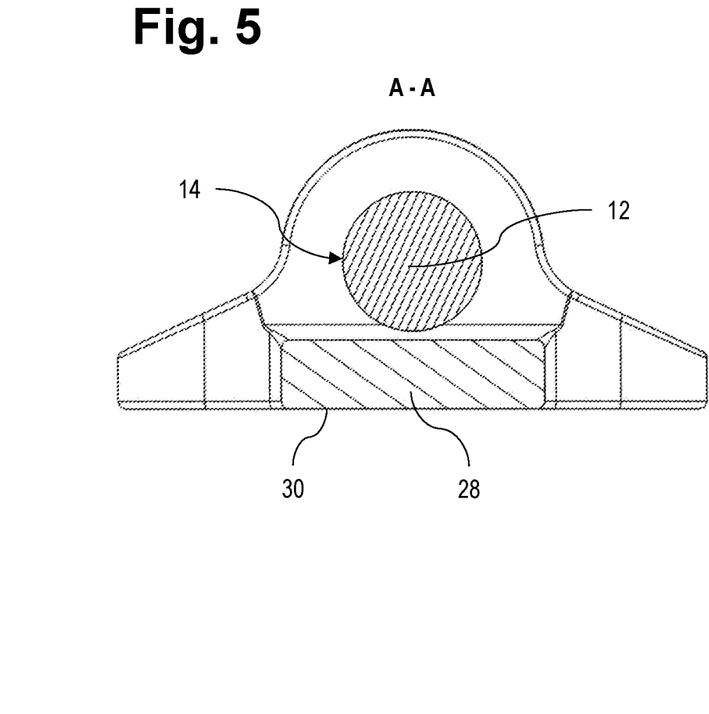
FIGS. 5 and 6 show, respectively, a cross-section A-A in between segments and a cross-section B-B through the center of a segment of the sternum closure device in FIG. 4.
Figure 6:
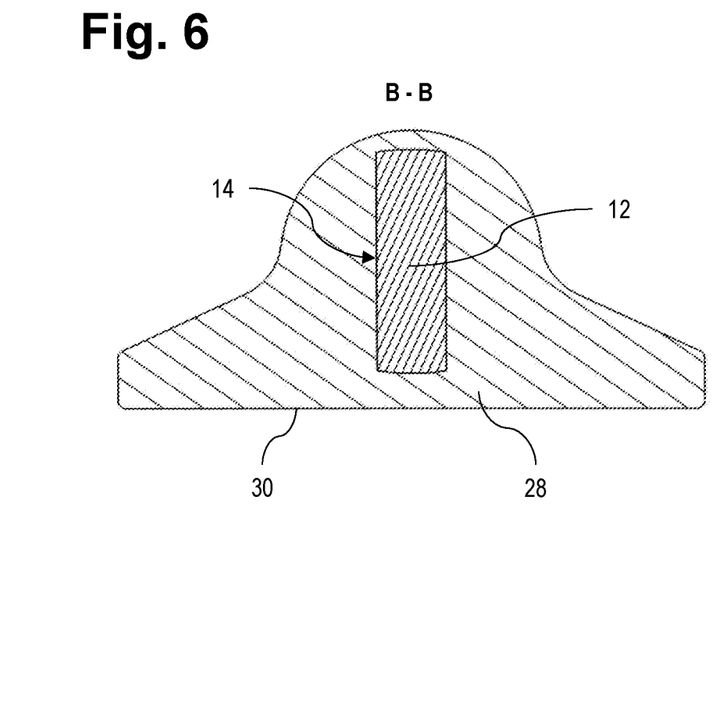

FIGS. 5 and 6 show, respectively, a cross-section A-A in between segments and a cross-section B-B through the center of a segment of the sternum closure device 2 as shown in FIG. 4.

As can be seen in FIG. 5, the cross-section of the wire 12 in between segments is uniform and corresponds to the cross-section of the wire 12 extending beyond the load distributor 10. However, towards the segment center, the wire 12 becomes narrow in the sides and, as can be seen in FIG. 6, extends in a top-bottom direction further than the cross-section of the uniform sections of the wire 12. As an example, the wire 12 may be locally deformed (e.g., stamped) to achieve a rectangular (or other non-circular) cross-section in a central segment region.

Further, it becomes apparent from FIG. 6 that a center of gravity of the load distributor 10 in a cross-section orthogonal to its longitudinal extension is off-centered from a center of the wire receiving section 14. This is achieved by the shown Ω-shaped cross-section of the load distributor 10, wherein the cross-section has smoothened transitions and rounded edges, and is closed at its basis.

The Ω-shape ensures a flat surface in form of the basis, which can be brought into contact with the sternum bone and distribute a compression force more evenly. Also, the smoothened transitions and rounded edges make an insertion of the load distributor 10 easier and safer, and the off-centered basis can be easily cut into a tapered V-shape at each end of the load distributor 10 without damaging the wire receiving section 14, which is further described below.

Figures 7, 8:
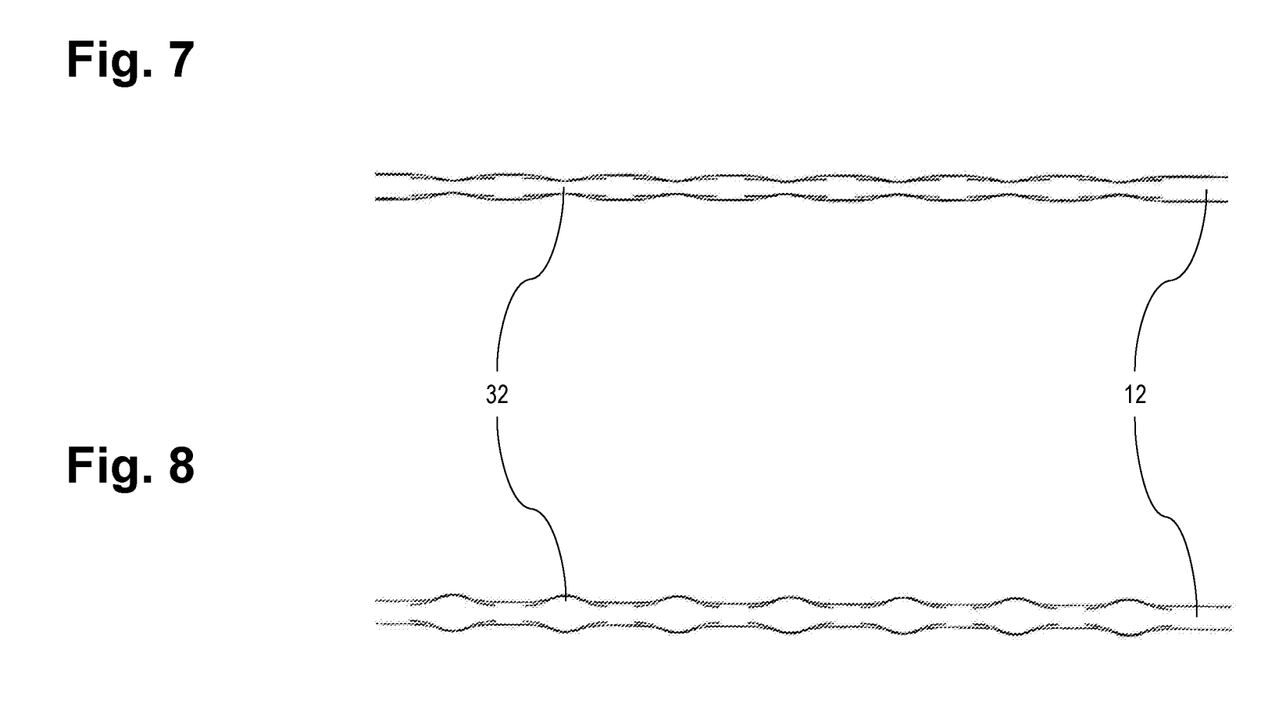
FIGS. 7 and 8 show, respectively, a top, and a side view of only the wire used in the sternum closure device in FIG. 4.

FIGS. 7 and 8 show, respectively, a top and a side view of only the wire 12 used in the sternum closure device in FIGS. 4 to 6. The protrusions of the wire 12 in the top-bottom direction and the indentations of the wire 12 in the sides within the segments form features 32, which serve to better hold the segments 20, 22i-22n, 24 thereon and avoid a displacement of the load distributor 10 on the wire 12, regardless of whether the load distributor 10 is molded over the wire 12 or the wire 12 inserted through the load distributor 10 in order to frictionally or adhesively engage with the wire receiving section 14.

Figure 9:
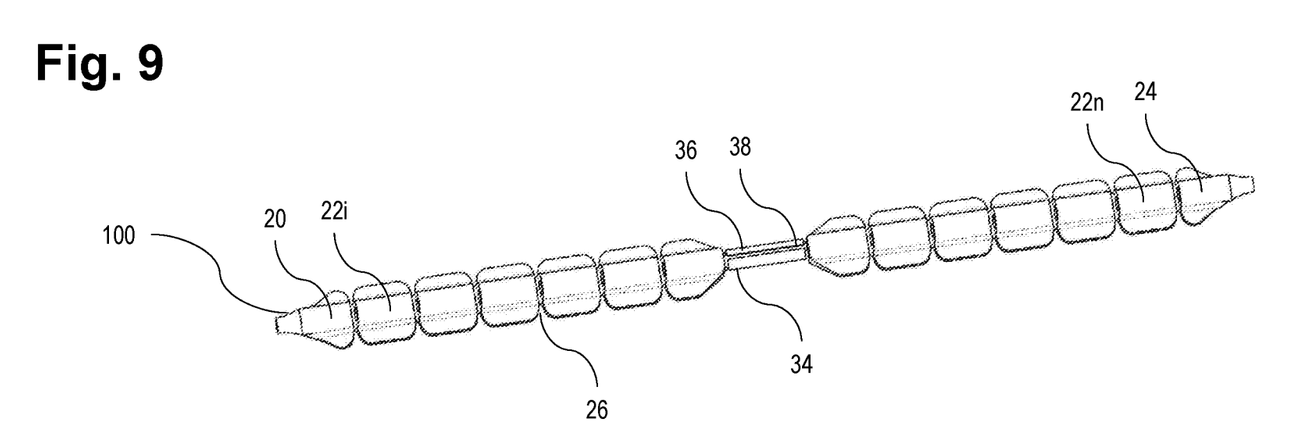
FIG. 9 shows a perspective top view of a crimpable load distributor according to a second embodiment.

FIG. 9 shows a perspective top view of a crimpable load distributor 100 according to a second embodiment. This load distributor 100 has a crimpable sleeve 34 substantially defining the first cross-sectional dimension. The sleeve 34 is arranged in between two equally long portions of a segment row (as explained above with reference to FIGS. 1 to 8). The sleeve 34 is overmolded by the segment rows at their respective innermost segments. These overmolded segments are tapered towards each other towards the sleeve 34. The particular shape of the sleeve 34 and interconnection with the respective segments of the segment row will become apparent from the following description of FIG. 10 in conjunction with FIG. 9.

Figure 10:
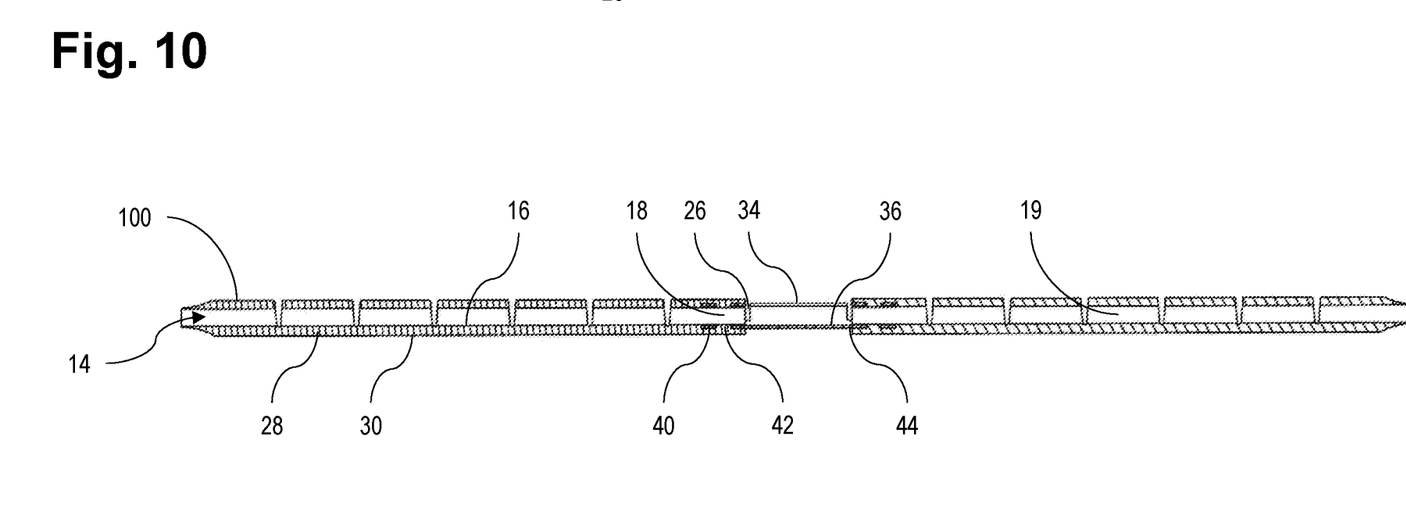
FIG. 10 shows a longitudinal side cross-section of the load distributor in FIG. 9.

FIG. 10 shows a longitudinal side cross-section of the sleeve 34 and load distributor 100 in FIG. 9. The load distributor 10 discussed above in connection with FIGS. 1 to 8 has a similar cross-sectional appearance.

The sleeve 34 in the load distributor 100 illustrated in FIGS. 9 and 10 comprises an elongated C-shaped part 36 having a slit or gap 38 extending along the longitudinal direction of the load distributor 100. The C-shaped part 36 lies between two rings 40 having openings 42 which in the variant shown in FIG. 10 are equally distanced from each other. Only two opposite openings 42 are visible in FIG. 10, the top and the bottom opening 42. The C-shaped part 36 and the rings 40 are connected by a bridge part 44 formed only on a portion of the C-shaped part 36 over less than 180° and symmetrically opposite the gap of the C-shaped part 36. While the bridge part 44 is arranged closest to the bone-contacting region 30, the gap 38 is opposite and furthest away from the bone-contacting region 30. In order to avoid direct contact of the metal sleeve 34 and the sternum bone, the sleeve 34 is offset from the bone-contacting region 30 of the load distributing section 28 towards the inside of the load distributor 100. At least one of the cylinders 40 of the sleeve 34 defines the through hole 18 as an opening for receiving the wire 12, and the load distributing section 28 has the through hole 19 as a wire receiving region 19 that forms an extension of the opening 18 of the sleeve 34.

Figure 11:
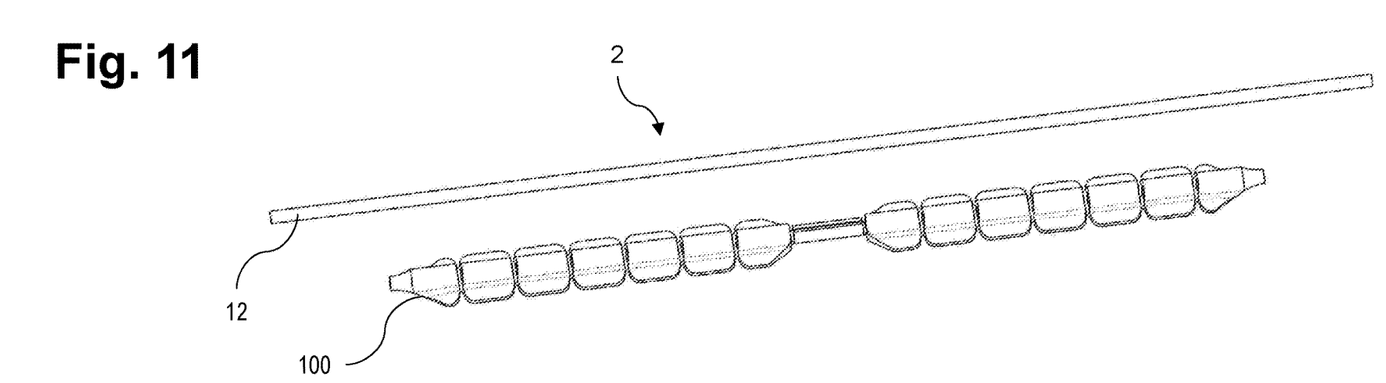
FIGS. 11 to 13 show, respectively, a sternum closure device with the crimpable load distributor in FIG. 9 and a uniform cross-section wire, an assembled state of the sternum closure device, and a longitudinal side cross-section of the assembled sternum closure device.
Figure 12:
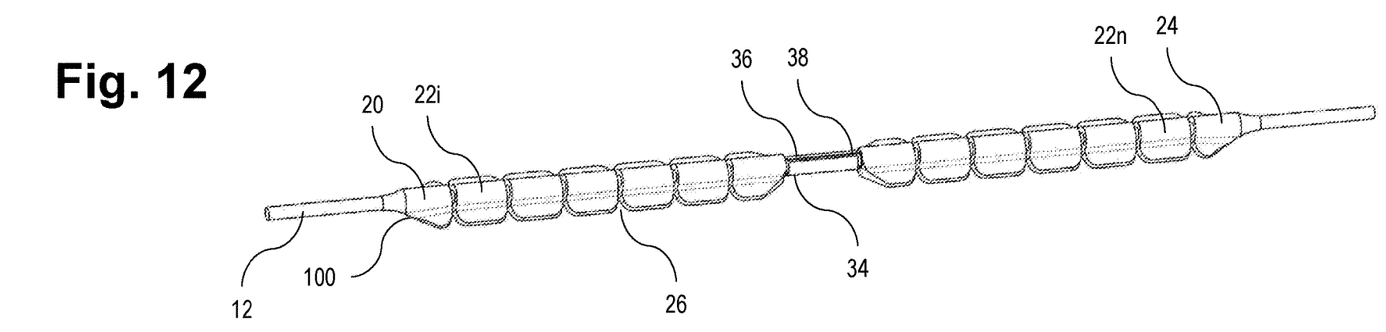
Figure 13:
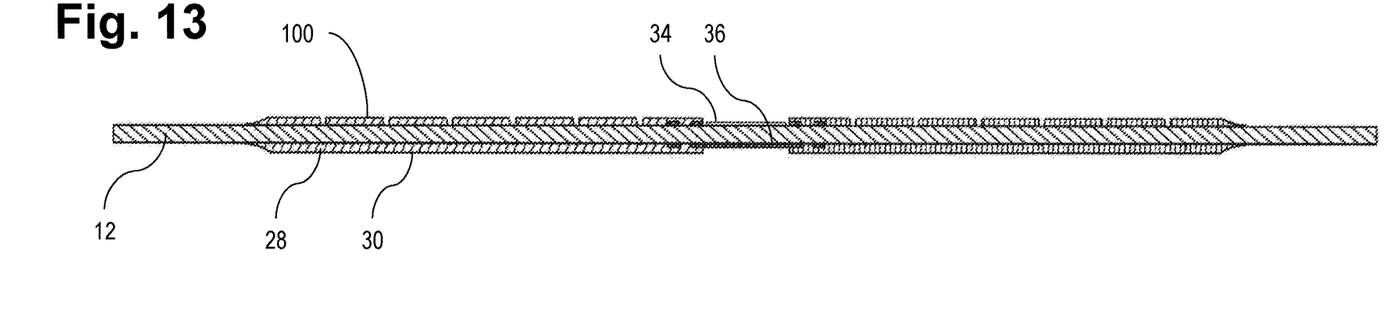

FIGS. 11 to 13 show, respectively, a sternum closure device 2 with the crimpable load distributor 100 in FIG. 9 and a uniform cross-section wire 12, an assembled state of the sternum closure device 2, and a longitudinal side cross-section of the assembled sternum closure device 2. While the wire 12 is shown to have a uniform cross-section, it will be appreciated that non-uniform cross-sections could be used as well (e.g., as shown in FIGS. 7 and 8).

FIGS. 12 and 13 show the sternum closure device with the load distributor 100 having the sleeve 34 of the wire receiving section 14 crimped around the wire 12. The crimping may be performed by surgical personal (e.g., a surgeon) in preparation of or during a surgical procedure in which the sternum closure device 2 is implanted. As such, the surgical personal may first thread the wire 12 through the load distributor 100 and then crimp the load distributor 100 to the wire 12 by locally exerting pressure on the load distributor 100 in the region the crimpable sleeve 34 using a suitable tool.

Figure 14:
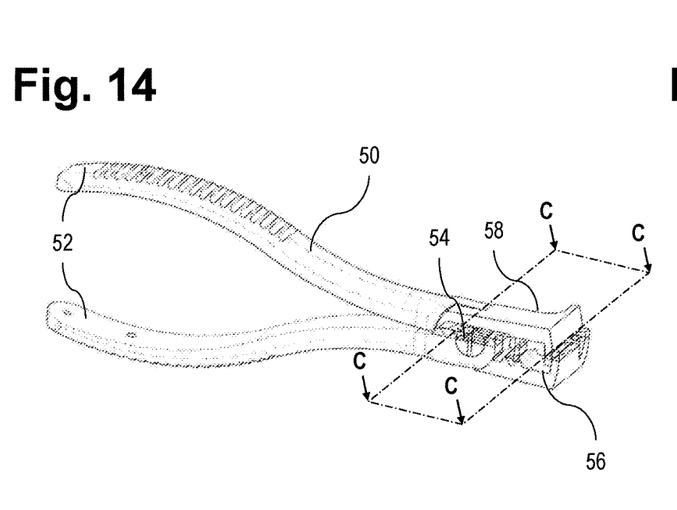
FIG. 14 shows a perspective view of a tool according to an embodiment.

FIG. 14 shows a perspective view of a tool 50 according to a third embodiment. The tool 50 has a pair of riffled handles 52, a pivot 54, and a pair of L-shaped jaws 56, 58. The tool 50 will be used by surgical personal to cut the load distributor 10, 100 (e.g., to "skin" on or more load distributor segments from the wire 12) and/or to crimp the sleeve 34 onto the wire 12.

Figure 15:
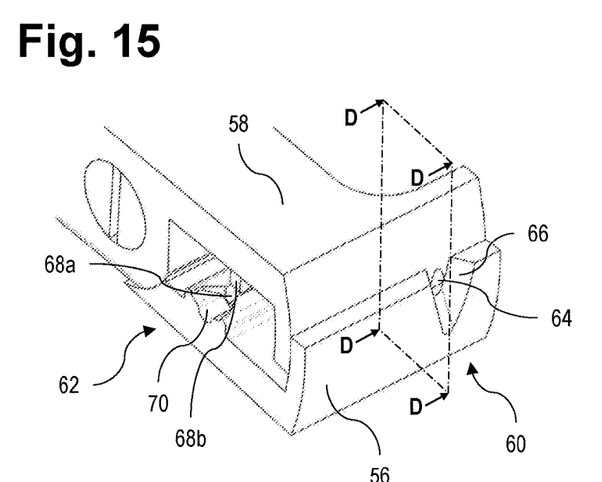
FIG. 15 shows an enlarged perspective view of a jaw section of the tool in FIG. 14.

FIG. 15 shows an enlarged perspective view of a jaw section of the tool 50 in FIG. 14. In this view it is visible that the jaw section has a cutting and skinning section 60 and a crimping section 62. The crimping section 62 has a symmetrical recess 68a on one jaw 56 and a complementary protrusion 68b on the other jaw 58. The recess 68a has tapered end parts 70 such that it corresponds to the outer shape of the sleeve 34 and the tapered segments of the load distributor 100 closest to the sleeve 34 (see, e.g., FIGS. 1, 4, and 9).

The pair of jaws 56, 58 is movable between a first load distributor receiving position and a second load distributor cutting position, wherein, in the second position, the jaws 56, 58 overlap in a longitudinal extension of the tool 50 and leave a clearance hole 64. Both jaws 56, 58 have substantially V-shaped cutting edges 66 which are tapered towards the other jaw 58, 56 at an angle along the longitudinal extension of the tool 50, see FIG. 17.

Figure 16:
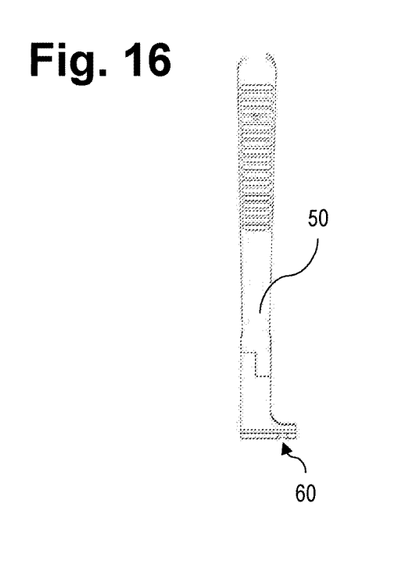
FIG. 16 shows a top view of the tool in FIG. 14.

FIG. 16 shows a top view of the tool 50 in FIG. 14. This view particularly shows that the jaws 56, 58 are L-shaped in the longitudinal extension of the tool 50.

Figure 17:
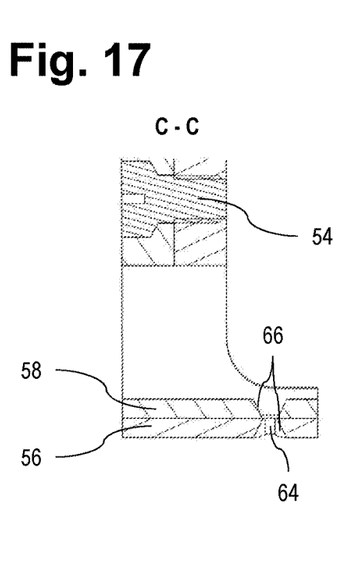
FIGS. 17 and 18 show, respectively, a top cross-section C-C through the jaw section of the tool in FIG. 14 without the crimping section and a side cross-section D-D through a cutting section of the jaw section in FIG. 15.
Figure 18:
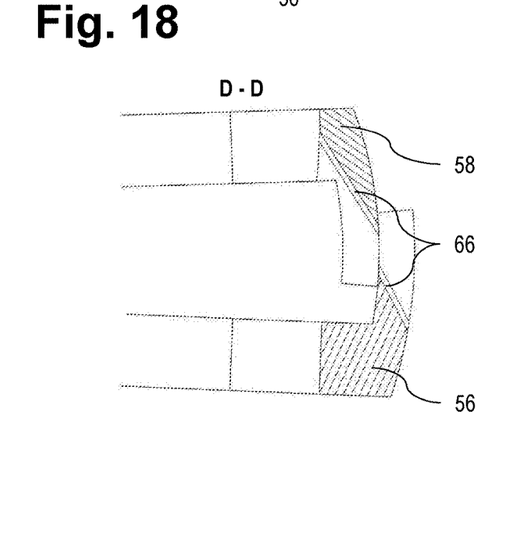

FIGS. 17 and 18 show, respectively, a top cross-section C-C through the jaw section of the tool 50 in FIG. 14 without the crimping section 6, and a side cross-section D-D through the skinning and cutting section 60 of the jaw section in FIG. 15. Particularly, the above-mentioned mentioned tapered V-shape of the cutting edges 66 is shown by the combination of FIGS. 17 and 18.

Next, the crimping section 62 will be explained in greater detail.

Figure 19:
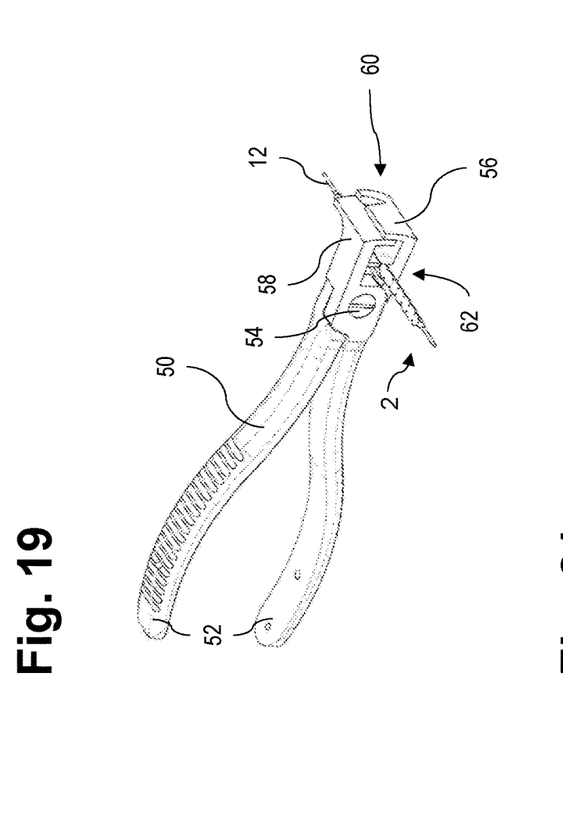
FIG. 19 shows a perspective view of a sternum closure system with the tool in FIG. 14 and a sternum closure device placed in a crimping section of the tool.

FIG. 19 shows a perspective view of a sternum closure system with the tool 50 in FIG. 14 and a sternum closure device placed in the crimping section 62 of the tool 50. The crimping section 62 is located on the jaws 56, 58 and between the pivot 54 and the cutting and skinning section 60. The crimping section 62 further extends in parallel to the pivot 54 and is located along the main longitudinal extension of the tool 50.

Figure 20:
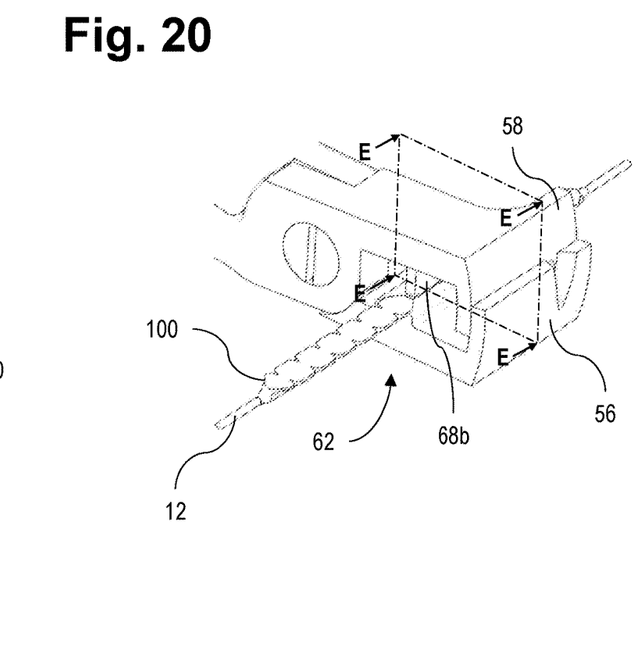
FIGS. 20 and 21 show, respectively, an enlarged perspective view of the jaw section of the sternum closure system in FIG. 19 and a side cross-section E-E through the jaw section with only the crimping section of the tool in FIG. 20.
Figure 21:
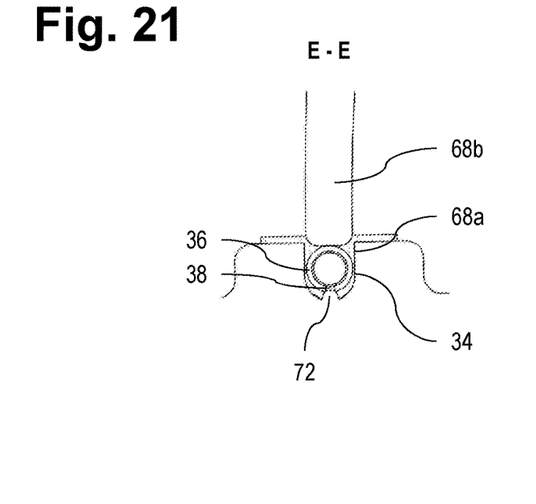

FIGS. 20 and 21 show, respectively, an enlarged perspective view of the jaw section of the sternum closure system in FIG. 19, and a side cross-section E-E through the jaw section with only the crimping section 62 of the tool 50 in FIG. 20.

FIG. 20 shows that the load distributor 100 fits into the recess 68a with the tapered end parts 70, which are indicated in FIG. 15. The tapered end parts 70 have the same inclination as the pair of cutting edges 66 in the second position of the jaws 56, 58 along the longitudinal extension of the tool 50.

FIG. 21 shows the sleeve 34 placed inside the recess 68a, such that the C-shaped part 36 is abutted by the recess 68a with the gap 38 pointing to the bottom of the recess 68a and enclosing a central trapezoid protrusion 72, which becomes narrow in a direction away from the bottom of the recess 68a and towards the protrusion 68b on the other jaw 58. The trapezoid protrusion 72 fixes the sleeve 34 in the shown position and further improves the crimpability of the sleeve 34.

Now, the cutting and skinning section 60 will be explained in greater detail.

Figure 22:
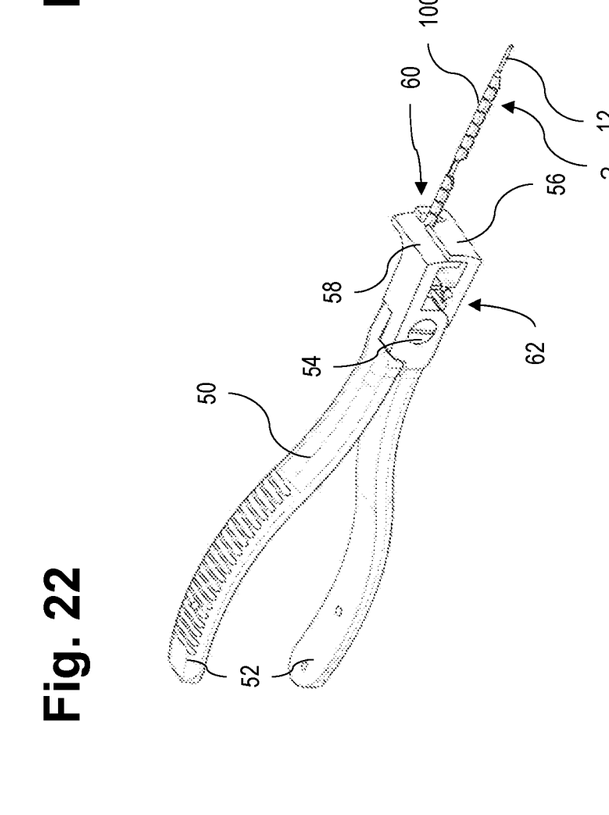
FIG. 22 shows a perspective view of the sternum closure system in FIG. 19 with a sternum closure device placed in the cutting section of the tool.

FIG. 22 shows a perspective view of the sternum closure system in FIG. 19 with a sternum closure device 2 placed in the cutting and skinning section 60 of the tool 50. The cutting and skinning section 60 is off-centered from the longitudinal extension direction of the tool 50.

Figure 23:
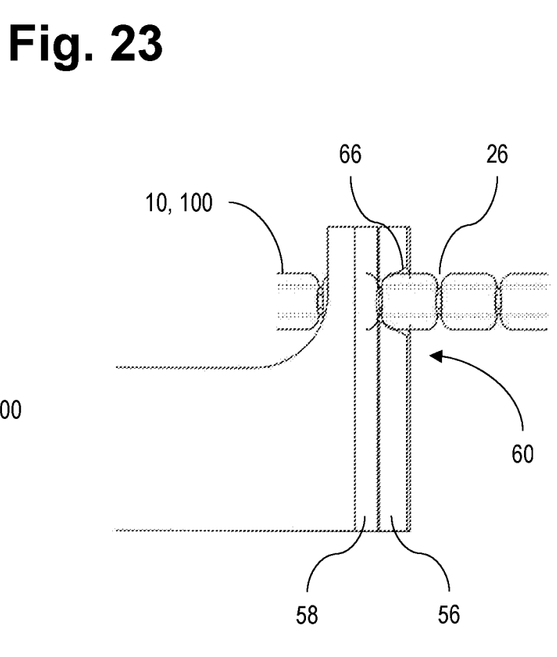
FIGS. 23 and 24 show, respectively, an enlarged top view of the sternum closure system in FIG. 22, and a top view of the sternum closure device in FIG. 22 with the left end of the left half of the load distributor cut and skinned from the wire, such that a V-shaped tapered segment is formed.
Figure 24:
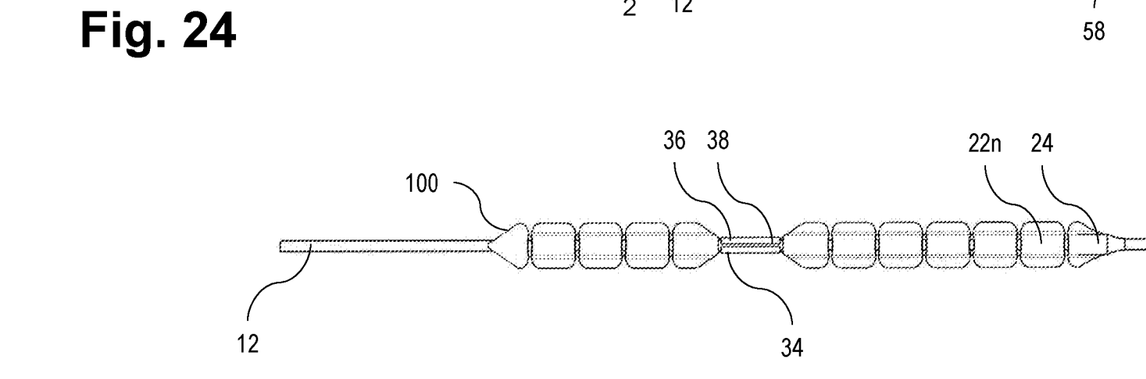

FIGS. 23 and 24 show, respectively, an enlarged top view of the sternum closure system in FIG. 22, and a top view of the sternum closure device in FIG. 22 with the left end, i.e., segments 20 and 22i, of the load distributor 100 cut and skinned from the wire 12, such that a V-shaped tapered segment is formed and remains as the outermost segment to the left. Using a suitable segment marking the outermost segment to the right can easily be identified and cut as well to achieve a symmetric cutting of the load distributor 100 at its two opposite ends.

FIG. 23 shows that the displacement of the jaws 56, 58 allow the user to better recognize the place of cutting, such that equal lengths of segments on both sides of the sleeve 34 can be achieved. Also, the indentations 26 between the (optional) segments 20, 22i-22n, 24 allow an easier, more precise and fixed placement of any one of the load distributors 10, 100 into the cutting edges 66 of one jaw 56, such that each rectangular segment 20, 22i-22n, 24 is cut into the same tapered shape shown in FIG. 24.

FIG. 24 shows a state in which the left part of the left half of the load distributor 100 has been cut and skinned from the wire 12, such that the outermost left segment is cut in a tapered shape, similar to the initial tapered shape of the segment 20. In a next step, the right part of the right half of the load distributor 100 will be cut and skinned from the wire 12 at the same distance from the sleeve 34 as the left half previously in order to shorten the load distributor 100 and adjust its length to the sternum bone, but still keep it symmetrical with regard to the sleeve 34.

The previously described embodiments of a load distributor 10, 100 may be combined as desired. The different embodiments merely serve to illustrate various aspects of the present disclosure.

While the present disclosure has been described with reference to exemplary embodiments, it will be appreciated that the present invention is not limited to what has been described above. For example, it will be appreciated that the dimensions of the parts may be varied as needed. Accordingly, it is intended that the present invention may be limited only by the scope of the claims appended hereto.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A load distributor for a sternum closure device, the load distributor comprising:
a wire receiving section configured to be attached to a wire of the sternum closure device, the wire receiving section having a first cross-sectional dimension; wherein the wire receiving section comprises at least one seperate and distinct crimpable sleeve received in the first cross-sectional dimension; and
a load distributing section configured to extend between a sternum bone and the wire, the load distributing section having a bone-contacting region and being made from a flexible material to conform to an outer surface of the sternum bone upon tightening of the wire, wherein the bone-contacting region has a second extension substantially perpendicular to the wire receiving section that exceeds the first cross-sectional dimension,
wherein the load distributing section comprises segments defining the bone-contacting region, wherein at least some of the segments have a rectangular shape.

2. The load distributor according to claim 1, wherein the at least one separate and distinct crimpable sleeve defines an opening for receiving the wire, and wherein the load distributing section has a wire receiving region that forms an extension of the opening of the at least one separate and distinct crimpable sleeve.

3. The load distributor according to claim 1, wherein the at least one separate and distinct crimpable sleeve is molded to the load distributing section.

4. The load distributor according to claim 1, wherein the segments are separated from each other by indentations in the load distributing section.

5. The load distributor according to claim 1, wherein the segments define a segment row with two opposite end segments, wherein segments having the same distance from their next end segment have an identical marking, and segments having different distances from their next end segment have different markings.

6. A sternum closure device, comprising:
a wire essentially defining the first cross-sectional dimension; and
the load distributor according to claim 1.

7. The sternum closure device according to claim 6, wherein the wire receiving section comprises the at least one seperate and distinct crimpable sleeve that is crimped or provided for being crimped around the wire.

8. The sternum closure device according to claim 6, wherein the load distributor is molded around the wire.

9. A sternum closure system comprising:
the load distributor according to claim 1;
a wire defining the first cross-sectional dimension of the load distributor; and
a tool for cutting the load distributor, the tool comprising:
a pair of jaws movable between a first load distributor receiving position and a second load distributor cutting position, wherein, in the second position, the jaws overlap in a longitudinal extension of the tool, and wherein the jaws define V-shaped cutting edges that taper at an angle along the longitudinal extension of the tool.

10. The system of claim 9, wherein the jaws of the tool leave a clearance hole in the second position, wherein the clearance hole substantially corresponds to the first cross-sectional dimension of the wire receiving section.

11. A load distributor for a sternum closure device, the load distributor comprising:
a wire receiving section configured to be attached to a wire of the sternum closure device, the wire receiving section having a first cross-sectional dimension; and
a load distributing section configured to extend between a sternum bone and the wire, the load distributing section having a bone-contacting region and being made from a flexible material to conform to an outer surface of the sternum bone upon tightening of the wire, wherein the bone-contacting region has a second extension substantially perpendicular to the wire receiving section that exceeds the first cross-sectional dimension,
wherein the load distributing section comprises segments defining the bone-contacting region, wherein the segments define a segment row with two opposite end segments, wherein segments having the same distance from their next end segment have an identical marking, and segments having different distances from their next end segment have different markings.

12. The load distributor according to claim 11, wherein the wire receiving section comprises at least one crimpable sleeve defining the first cross-sectional dimension.

13. The load distributor according to claim 12, wherein the sleeve defines an opening for receiving the wire, and wherein the load distributing section has a wire receiving region that forms an extension of the opening of the at least one crimpable sleeve.

14. The load distributor according to claim 12, wherein the at least one crimpable sleeve is molded to the load distributing section.

15. The load distributor according to claim 11, wherein the segments are separated from each other by indentations in the load distributing section.

16. A sternum closure device, comprising:
a wire essentially defining the first cross-sectional dimension; and
the load distributor according to claim 11.

17. The sternum closure device according to claim 16, wherein the wire receiving section comprises at least one crimpable sleeve that is crimped or provided for being crimped around the wire.

18. A sternum closure system comprising:
the load distributor according to claim 11;
a wire defining the first cross-sectional dimension of the load distributor; and
a tool for cutting the load distributor, the tool comprising:
a pair of jaws movable between a first load distributor receiving position and a second load distributor cutting position, wherein, in the second position, the jaws overlap in a longitudinal extension of the tool, and wherein the jaws define V-shaped cutting edges that taper at an angle along the longitudinal extension of the tool.

19. The system of claim 18, wherein the jaws of the tool leave a clearance hole in the second position, wherein the clearance hole substantially corresponds to the first cross-sectional dimension of the wire receiving section.

* * * * *